United States Patent [19]

Weber et al.

[11] Patent Number: 5,418,145
[45] Date of Patent: May 23, 1995

[54] PROCESS FOR THE PREPARATION OF 4-ANDROSTENE-3,17-DIONE AND 1,4-ANDROSTADIENE-3,17-DIONE

[75] Inventors: Alfred Weber; Mario Kennecke; Johannes Kurzidim, all of Berlin, Germany

[73] Assignee: Schering Aktiengesellschaft, Berlin and Bergkamen, Germany

[21] Appl. No.: 150,346

[22] Filed: Nov. 10, 1993

Related U.S. Application Data

[63] Continuation of Ser. No. 909,506, Jun. 30, 1992, abandoned, which is a continuation of Ser. No. 574,856, Aug. 30, 1990, abandoned, which is a continuation of Ser. No. 110,761, Aug. 12, 1987, abandoned.

[30] Foreign Application Priority Data

Dec. 13, 1985 [DE] Germany .................. 35 44 662.5

[51] Int. Cl.⁶ .......................... C12N 1/20; C12P 33/16
[52] U.S. Cl. ............................ 435/55; 435/253.1
[58] Field of Search ................ 435/55, 52, 865, 863, 435/253.1, 253.2

[56] References Cited

U.S. PATENT DOCUMENTS

| | | | |
|---|---|---|---|
| 3,684,657 | 8/1972 | Kraychy | 435/55 |
| 3,759,791 | 9/1973 | Marsheck | 435/55 |
| 4,345,029 | 8/1982 | Woucha et al. | 435/55 |

FOREIGN PATENT DOCUMENTS

| | | | |
|---|---|---|---|
| 7152898 | 9/1982 | Japan | 435/55 |

OTHER PUBLICATIONS

Goodfellow et al., *The Biology of Actinomycetes* Academic Press, 1984.

*Primary Examiner*—Irene Marx
*Attorney, Agent, or Firm*—Millen, White, Zelano, & Branigan

[57] ABSTRACT

A process is claimed for the preparation of 4-androstene-3,17-dione and 1,4-androstadiene-3,17-dione of the general formula

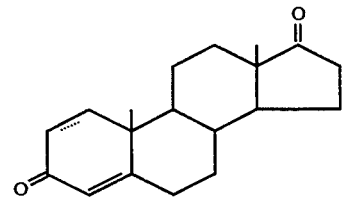

wherein --- symbolizes a single bond or a double bond, characterized by fermenting α-sitosterol

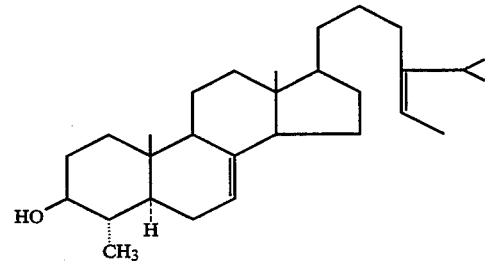

with a culture of a strain of microorganisms capable of side chain degradation of sterols.

2 Claims, No Drawings

PROCESS FOR THE PREPARATION OF 4-ANDROSTENE-3,17-DIONE AND 1,4-ANDROSTADIENE-3,17-DIONE

This application is a continuation of application Ser. No. 07/909,506 filed June 30, 1992, now abandoned, which is a continuation of application Ser. No. 07/574,856, filed August 30, 1990, now abandoned, which is a continuation of application Ser. No. 07/110,761 filed August 12, 1987, now abandoned.

The invention relates to the process characterized in the claims.

It is known that numerous microorganisms (thus, for example, those of the genera Arthrobacter, Brevibacterium, Microbacterium, Protaminobacter, Bacillus, Nocardia, Streptomyces and, in particular, Mycobacterium) possess the natural ability of degrading naturally occurring $3\beta$-hydroxy-$\Delta^5$-sterols (such as cholesterol or sitosterol) to carbon dioxide and water, and that 4-androstene-3,17-dione and 1,4-androstadiene-3,17-dione are formed intermediarily during this degradation.

It is furthermore known that it is possible with the aid of inhibitor additives or mutated microorganisms to regulate the degradation of the sterols in such a way that degradation of the thus-formed 4-androstene-3,17-dione or 1,4-androstadiene-3,17-dione is avoided (see German Laid-Open Applications 15 43 269 and 15 93 327, as well as U.S. Pat. No. 3,684,657).

It is surprising to one skilled in the art that, under the conventional conditions, the side chain of $\alpha$-sitosterol is likewise degraded, for it is known that the side chain degradation of sterols is brought about by a very complex fermentation system, and it could not be expected that all of the enzymes participating in side chain degradation of natural steroids have the capability also effect side chain degradation of this compound. Moreover, it could not be foreseen that, in this degradation, the $\Delta^7$-double bond of $\alpha$-sitosterol is hydrogenated and the methyl group in the $4\beta$-position is split off.

Apart from the use of different starting compounds, the process of this invention is performed under the same fermentation conditions likewise employed in the conventional microbiological side chain degradation reactions of sterols.

According to this invention, fermentation is conducted with the use of the microorganism culture customarily utilized for side chain degradation of sterols. Suitable cultures are, for example, bacterial cultures capable of side chain degradation of sterols of the genera Arthrobacter, Brevibacterium, Microbacterium, Protaminobacter, Streptomyces or, in particular, the genus Mycobacterium. Examples of suitable microorganisms are: *Microbacterium lactum* IAM-1640, *Protaminobacter alboflavus* IAM-1040, *Bacillus roseus* IAM-1257, *Bacillus sphaericus* ATCC-7055, *Nocardia gardneri* IAM-105, *Nocardia minima* IAM-374, *Nocardia corallina* IFO-3338, *Streptomyces rubescens* IAM-74 or, in particular, the microorganisms *Mycobacterium avium* IFO-3082, *Mycobacterium phlei* IFO-3158, *Mycobacterium phlei* (Institute of Health, Budapest No. 29), *Mycobacterium phlei* ATCC-354, *Mycobacterium smegmatis* IFO-3084, *Mycobacterium smegmatis* ATCC-20, *Mycobacterium smegmatis* (Institute of Health, Budapest No. 27), *Mycobacterium smegmatis* ATCC-19979, and *Mycobacterium fortuitum* CBS-49566.

Especially preferred microorganisms are *Mycobacterium spec.* NRLL B-3805, *Mycobacterium spec.* NRRL B-3683, *Mycobacterium phlei* NRRL B-8154, and *Mycobacterium fortuitum* NRRL B-8153, making it possible $\alpha$-sitosterol without the use of additional inhibitors impeding the $9\alpha$-hydroxylation.

Under the culturing conditions usually employed for these microorganisms, submerged cultures are grown in a suitable nutrient medium under aeration. Then the substrate (dissolved in a suitable solvent or preferably in emulsified form) is added to the cultures, and fermentation is conducted until maximum substrate conversion has been attained.

Suitable substrate solvents are, for example, methanol, ethanol, glycol monomethylether, dimethylformamide or dimethylsulfoxide. Emulsification of the substrate can be effected by introducing the latter in micronized form or dissolved in a water-miscible solvent (such as methanol, ethanol, acetone, glycol monomethyl ether, dimethylformamide or dimethyl sulfoxide) under strong turbulence via nozzles into (preferably demineralized) water containing the usual emulsifying aids. Suitable emulsifying aids are nonionic emulsifiers, such as, for example, ethylene oxy adducts or fatty acid esters of polyglycols. Examples of suitable emulsifiers that can be cited are the commercial surfactants "Tegin", "Tween" and "Span".

The optimum substrate concentration, time of adding substrate, the duration of fermentation are dependent on the structure of the substrate used and on the type of microorganism employed. These data, as is generally required in microbiological steroid conversions, must be determined in the individual case by preliminary experiments, with which a person skilled in the art is familiar.

The 4-androstene-3,17-dione derivatives of general Formula I producible according to the process of this invention are, as is known, valuable intermediates presently utilized commercially for the synthesis of pharmacologically active steroids.

The examples set forth below serve for describing the process of this invention.

EXAMPLE 1

A 2-liter Erlenmeyer flasks with 500 ml of a sterile nutrient medium containing

1% of yeast extract
0.45% of disodium hydrogen phosphate
0.34% of potassium dihydrogen phosphate and
0.2% of "Tween" 80
adjusted to pH 6.7 is inoculated with a suspension of a dry culture of *Mycobacterium spec.* NRRL B-3805 and shaken at 30° C. at 190 rpm for 3 days.

Ten Erlenmeyer flasks (500 ml) with 100 ml of sterile nutrient medium each, containing 2.5% of corn steep liquor
0.3% of diammonium hydrogen phosphate
0.25% of soybean meal and
0.25% of "Tween" 80
adjusted to pH 7.0 are respectively inoculated with 5 ml of the *Mycobacterium spec.* germination culture and shaken at 30° C. at 220 rpm for 24 hours. Then, 100 mg of $\alpha$-sitosterol, dissolved in 3.0 ml of dimethylformamide, is added to each culture, and fermentation is continued for another 96 hours at 30° C.

The combined cultures are extracted with ethylene chloride, the extract is concentrated under vacuum, and the residue is purified by chromatography over a silica gel column, thus obtaining, after recrystallization from diisopropyl ether, 160 mg of 4-androstene-3,17-dione.

In addition, 385 mg of unreacted α-sitosterol is recovered.

EXAMPLE 2

Under the conditions of Example 1, but using *Mycobacterium spec.* NRRL B-3683, 1,000 mg of α-sitosterol in total is reacted, worked up, and yields 140 mg of 1,4-androstadiene-3,17-dione besides 630 mg of unconverted α-sitosterol.

We claim:

1. A process for the preparation of 4-androstene-3,17-dione, comprising fermenting α-sitosterol with *Mycobacterium spec.* NRRL B-3805, and isolating the thus-produced 4-androstene-3,17-dione.

2. A process for the preparation of 1,4-androstadiene-3,17-dione, comprising fermenting α-sitosteroi with *Mycobacterium spec.* NRRL B-3683, and isolating the thus-produced 1,4-androstadiene-3,17-dione.

* * * * *